United States Patent [19]

Hidaka et al.

[11] 4,447,210
[45] May 8, 1984

[54] UPPER STRUCTURE FOR ARTIFICIAL APATITE DENTAL ROOT

[75] Inventors: Tsuneo Hidaka; Masahide Inoue; Makoto Ogiso, all of Tokyo, Japan

[73] Assignee: Asahi Kogaku Kogyo Kabushiki Kaisha, Tokyo, Japan

[21] Appl. No.: 450,156

[22] Filed: Dec. 15, 1982

[30] Foreign Application Priority Data

Dec. 17, 1981 [JP] Japan .................................. 56-204134

[51] Int. Cl.³ .............................................. A61C 8/00
[52] U.S. Cl. ...................................... 433/173; 433/169; 433/218
[58] Field of Search ............... 433/169, 173, 218, 222; 128/92 C, 92 CA; 3/1.9, 1.91, 1.911, 1.912, 3/1.913

[56] References Cited

U.S. PATENT DOCUMENTS

| | | | |
|---|---|---|---|
| 2,854,746 | 10/1958 | Lester et al. | 433/169 |
| 2,880,508 | 4/1959 | Lester et al. | 433/169 |
| 3,197,866 | 8/1965 | Barron | 433/169 |
| 3,722,094 | 3/1973 | Rivoir | 433/169 |
| 3,723,995 | 4/1973 | Baumann | 128/92 CA |
| 3,827,145 | 8/1974 | Richards | 433/175 |
| 3,955,280 | 5/1976 | Sneer | 433/169 |
| 3,991,472 | 11/1976 | Lukesch | 433/169 |
| 4,215,986 | 8/1980 | Riess | 433/173 |
| 4,290,755 | 9/1981 | Scott | 433/173 |
| 4,318,696 | 3/1982 | Kasama et al. | 433/173 |

*Primary Examiner*—John J. Wilson
*Attorney, Agent, or Firm*—Sughrue, Mion, Zinn, Macpeak and Seas

[57] ABSTRACT

An upper structure for an artificial apatite dental root is disclosed. The structure includes inner and outer crowns having a buffer element placed therebetween. The buffer element serves as a satisfactory substitute for the periodontal membrane of a natural tooth.

3 Claims, 1 Drawing Figure

UPPER STRUCTURE FOR ARTIFICIAL APATITE DENTAL ROOT

BACKGROUND OF THE INVENTION

The present invention relates to an upper structure for an aritificial apatite dental root.

Among the conventional prosthodontical methods used to restore the oral function damaged by missing teeth is direct implantation of an artificial prosthesis in the affected area. Although several materials have been developed for use in this implantation technique, few have the necessary high bioaffinity with the jaw tissues and remain stable during mastication. Among the few exceptions is a sintered product of apatite. An aritificial dental root made of sintered apatite is based on calcium and phosphorus, and because its composition is almost the same as natural aptite, it has a very high bio-affinity with the jaw tissue. In an experiment with dogs, an artificial apatite dental root underwent complete synosteosis in two months after implantation. A natural tooth has a periodontal membrane between the root and the jaw tissue, which membrane is said to have the ability to buffer an external load on the tooth. It is therefore necessary to provide an upper structure that provides a certain buffer mechanism for an implanted apatite dental root.

SUMMARY OF THE INVENTION

An object of the present invention is to provide an aritificial apatite dental root having an upper structure wherein a buffer member is inserted between the inner and outer crowns.

BRIEF DESCRIPTION OF THE DRAWING

The single FIGURE is a vertical sectional view of the artificial dental root of the present invention showing an upper structure mounted thereon.

DETAILED DESCRIPTION OF THE PREFERRED EMBODIMENT

Figure 1:
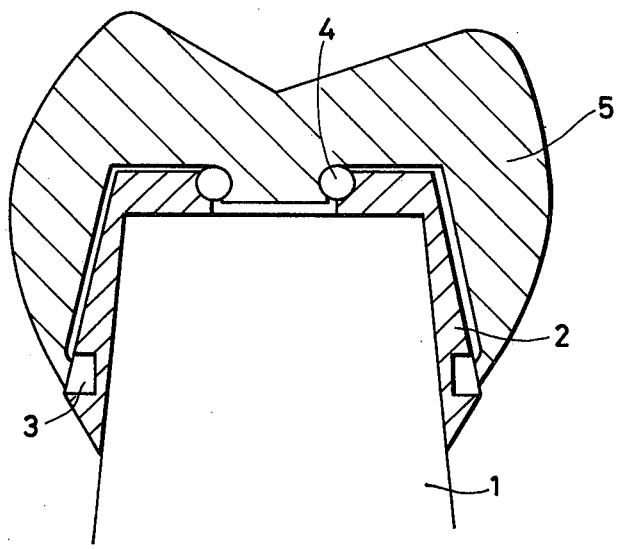

FIG. 1 is a vertical section of the artificial dental root of the present invention showing an upper structure mounted thereon. An artificial apatite dental root 1 has on its top an inner crown 2 made of a platinum-containing gold alloy having high ductility and malleability. The apatite dental root is bonded to the inner crown by a conventional dental cement composition. The purpose of the inner crown is to prevent the breakage of the dental root when it is hit by various dental instruments used within the oral cavity during impression making and trimming operations. Around the skirt of the inner crown is made a groove to retain a rectangular O-ring 3 made of an elastic material such as rubber. A recess is formed in the center of the top of the inner crown and a groove is made around this recess to retain an O-ring 4 having a circular cross section and also being made of an elastic material such as rubber. The inner crown is covered by an outer crown 5 with a given clearance between the two. The top of the outer crown contacts a mating tooth. A circular projection extends from the center of the inner top wall of the outer crown and a groove is made around this projection to retain the O-ring 4. The lower part of the outer crown bears against the periphery of the O-ring 3 fitted around the inner crown.

With the structure described above, the O-ring 3 provides a buffer against lateral pressure on the artificial apatite dental root 1, whereas the O-ring 4 provides a buffer against vertical pressure on the root. The outer crown 5 may be made of any known dental alloy.

The artificial dental root of the present invention is used in dentistry by the following method. First, an artificial apatite dental root of a predetermined size and shape is implanted in a socket. One or two months later, the implanted tooth is tapped, vibrated or the depth of its pocket is measured to see that it is firmly attached to the jaw bone. An impression is made or an X-ray photograph taken to check how the tooth bites with a mating tooth. The above data is the basis for the design of the upper structure to be mounted on the implanted dental root. The inner crown proper is made of a platinum-containing gold alloy. The inner crown is bonded to the root by dental cement. The O-ring with the rectangular cross section is fitted around the lower skirt of the inner crown, and the O-ring with the round cross section is mounted on the outer crown fabricated so as to provide good occlusion. The outer crown is then fitted over the inner crown. Articulating paper is used to closely check if precise occlusion is established, and if not, the outer crown is removed and trimmed. The upper structure according to the present invention has proved to be a satisfactory substitute for the periodontal membrane of a natural tooth.

What is claimed is:

1. An upper structure for an artificial apatite dental root comprising an inner crown having a lower skirt portion and an upper central recess adapted to be fixedly secured to said root, an outer crown having a lower portion adapted to overlie said skirt portion in spaced relation thereto and a downwardly extending projection adapted to extend into said central recess, an annular groove formed in the lower end of said skirt portion of said inner crown, a first annular elastic member secured in said groove with the lower end of said outer crown disposed in contact with said first elastic member, opposed grooves formed in said central recess of said inner crown and said projection of said outer crown and a second annular elastic member disposed in said opposed grooves whereby said first and second elastic members support said outer crown in spaced relation to said inner crown.

2. An upper structure for an artificial apatite dental root as set forth in claim 1 wherein said first annular elastic member has an outer surface which is substantially flush with the outer surface of said inner crown.

3. An upper structure for an artificial apatite dental root as set forth in claim 1 wherein said second elastic member is comprised of an O-shaped ring.

* * * * *